(12) United States Patent
Eagles et al.

(10) Patent No.: US 6,716,457 B1
(45) Date of Patent: Apr. 6, 2004

(54) EFFECTS OF BACTERICIDE (PERACETIC ACID-HYDROGEN PEROXIDE-WATER COMBINATION) TO AGRICULTURAL CHEMICALS IN BACTERIA CONTROL WHEN THEY ARE IN CONTACT WITH ONE ANOTHER

(75) Inventors: Karen L. Eagles, Raymore, MO (US); Donald W. Edson, Independence, MO (US); Kevin Park, Kansas City, MO (US); John G. Rogers, Kansas City, MO (US); John W. Brandriff, Blue Springs, MO (US); Stephen C. Slahck, Independence, MO (US)

(73) Assignee: Bayer Polymers LLC, Pittsburgh, PA (US)

( * ) Notice: Subject to any disclaimer, the term of this patent is extended or adjusted under 35 U.S.C. 154(b) by 0 days.

(21) Appl. No.: 09/690,781

(22) Filed: Oct. 17, 2000

(51) Int. Cl.$^7$ .................. A01N 59/00; A01N 37/02; A01N 43/707; A01N 43/653; A01N 43/40
(52) U.S. Cl. .................. 424/616; 424/405; 504/123; 504/124; 504/229; 504/358; 504/362; 514/229.2; 514/277; 514/341; 514/342; 514/356; 514/357; 514/365; 514/372; 514/383; 514/557; 514/937; 422/28; 422/29; 422/37; 422/41
(58) Field of Search .................. 424/616, 405; 504/123, 124, 229, 358, 362, 121; 514/229.2, 277, 341, 342, 356, 357, 365, 372, 383, 557, 937, 970; 422/28, 29, 37, 41

(56) References Cited

U.S. PATENT DOCUMENTS

| | | | |
|---|---|---|---|
| 4,051,049 A | 9/1977 | Elliott et al. | 252/51.5 |
| 4,297,298 A | 10/1981 | Crommelynck et al. | 260/502 R |
| 4,587,264 A | 5/1986 | Jourdan-Laforte et al. | 514/557 |
| 4,742,060 A | 5/1988 | Shiokawa et al. | 514/252 |
| 4,849,432 A | 7/1989 | Shiokawa et al. | 514/341 |
| 5,008,106 A | 4/1991 | Merianos et al. | 424/80 |
| 5,283,231 A | 2/1994 | Morgan et al. | 504/148 |
| 5,508,046 A | 4/1996 | Cosentino et al. | 424/616 |
| 5,656,302 A | 8/1997 | Cosentino et al. | 424/616 |
| 5,719,146 A | 2/1998 | Shiokawa et al. | 514/229.2 |
| 5,852,012 A | 12/1998 | Maienfisch et al. | 514/229.2 |
| 6,048,542 A | 4/2000 | Eagles et al. | 424/405 |
| 6,074,987 A | 6/2000 | Shafer et al. | 504/132 |
| 6,096,226 A | 8/2000 | Fuchs et al. | 210/759 |

FOREIGN PATENT DOCUMENTS

| | | |
|---|---|---|
| GB | 1 570 492 | 7/1980 |
| WO | 93/01822 | 2/1993 |

OTHER PUBLICATIONS

Block, Seymour S. Disinfection, Sterilization and Preservation. Lea & Febiger, Philadelphia, 4th ed, 1991, p. 176.*
Kirk–Othmer Encyclopedia of Chemical Technology, 4th ed., John Wiley & Sons, New York, 1993, pp. 256–257.*
CABA Abstract 78:64467 (1978).*
Knowles, D. A. et al., "Preservation of Agrochemicals," in: MOrpeth, Fraser F. Preservation of Surfactant Formulations, Blackie Glasgow (UK), 1995, pp. 118–146.*

\* cited by examiner

*Primary Examiner*—John Pak
(74) *Attorney, Agent, or Firm*—Joesph C. Gil; Raymond J. Harmuth

(57) ABSTRACT

The present invention relates to a process for inhibiting or eliminating the growth of microorganisms in pesticide suspensions. More particularly, the process of the present invention includes the addition of a combination of peracetic acid, hydrogen peroxide, and water to the pesticide suspension. Further, the process of the present invention includes the application of the peracetic acid, hydrogen peroxide, and water combination to the interior surface of the vessel in which the pesticide suspension is contained. Still further, the process of the present invention includes the application of the peracetic acid, hydrogen peroxide, and water combination to a surface in which the pesticide suspension is in contact.

38 Claims, No Drawings

EFFECTS OF BACTERICIDE (PERACETIC ACID-HYDROGEN PEROXIDE-WATER COMBINATION) TO AGRICULTURAL CHEMICALS IN BACTERIA CONTROL WHEN THEY ARE IN CONTACT WITH ONE ANOTHER

TECHNICAL FIELD OF THE INVENTION

The present invention relates to a process for inhibiting or eliminating the growth of microorganisms in pesticide suspensions. More particularly, the process of the present invention includes the addition of a combination of peracetic acid, hydrogen peroxide and water, to the pesticide suspension. Further, the process of the present invention includes the application of the peracetic acid, hydrogen peroxide, and water combination to the interior surface of the vessel in which the pesticide suspension is contained. Still further, the process of the present invention includes the application of the peracetic acid, hydrogen peroxide, and water combination to a surface in which the pesticide suspension is in contact.

BACKGROUND OF THE INVENTION

A pesticide suspension is a homogeneous mixture of small solid particles of pesticide suspended in a liquid medium. The growth of microorganisms in the pesticide suspension can cause a solid precipitate to form and therefore, a loss of homogeneity in the mixture. Formation of the precipitate and the loss of homogeneity can result in product failure due to non-uniform applications of the pesticide, and plugging of strainers and nozzles used with the application equipment.

Peracetic acid and hydrogen peroxide solutions are known in the art. French Patent No. 2,462,425, discloses a process for the preparation of stable dilute solutions of peracetic acid. U.S. Pat. No. 4,051,049 discloses a formulation having from 0.5 to 20% peracetic acid, 25 to 40% hydrogen peroxide and from 0 to 5% of an anionic surfactant. U.S. Pat. No. 5,656,302 discloses stable microbicidal formulations comprising a considerably greater quantity of peracetic acid plus acetic acid than the quantity of hydrogen peroxide.

Further, the use of peracetic acid and hydrogen peroxide solutions for purposes of sterilization and disinfection are well known. For example, commercial solutions of noncorrosive time-stable carboxylic peracids, particularly peracetic acid, are known to be useful for the sterilization and microbiological disinfection of equipment in the food industry (see U.S. Pat. No. 4,587,264). In addition to the food industry, commercial peracetic acid and hydrogen peroxide solutions are also known disinfectants in the medical and dental professions. U.S. Pat. No. 5,508,046 describes novel stable microbicides comprising hydrogen peroxide, peracetic acid, acetic acid, purified water, and a stabilizer having anticorrosive properties, for use in the sterilization of surgical and dental instruments.

Moreover, the commercial peracetic acid solution Minncare was developed by the Minntech Corporation and is used as a disinfectant in providing protection against short- and long-term bacterial problems for reverse osmosis membranes and their associated distribution systems.

To reduce or eliminate the growth of microorganisms in pesticide suspensions, a practice of combining or formulating the pesticide compounds with a preservative has developed in the art. U.S. Pat. No. 5,283,231 describes formaldehyde, sodium benzoate, glutaraldehyde, and pentachlorophenol, as effective preservatives to prevent microbial spoiling in low-melting dinitroaniline pesticide suspensions.

Not all preservatives are effective against all types of microorganisms, in all pesticide suspensions. Thus, there is a need in the art to determine specific preservatives that are effective in a particular flowable aqueous pesticide composition (i) to reduce or eliminate the growth of microorganisms, (ii) while being easy to handle during preparation and use, and (iii) maintaining an excellent shelf-life even during extended storage.

SUMMARY OF THE INVENTION

It is an object of the present invention to provide a process for inhibiting or eliminating the growth of microorganisms in pesticide suspensions. This and other objects which will be apparent to those skilled in the art are accomplished by the (i) addition of a combination of peracetic acid, hydrogen peroxide, and water to the pesticide suspension, or (ii) application of the peracetic acid, hydrogen peroxide, and water combination to the interior surface of the vessel in which the pesticide suspension is contained, or (iii) application of the peracetic acid, hydrogen peroxide, and water combination to a surface which the pesticide suspension is in contact. The peracetic acid, hydrogen peroxide, and water combination is present in the water-based pesticide suspension in an amount of from about 0.05% to about 1.0% by weight of the suspension.

DETAILED DESCRIPTION OF THE PREFERRED EMBODIMENTS OF THE INVENTION

The process of the present invention comprises (i) the addition of a combination of a peracetic acid, hydrogen peroxide, and water to a pesticide formulation; (ii) the application of a combination of peracetic acid, hydrogen peroxide, and water to the interior surface of the vessel in which the pesticide formulation is contained; and (iii) the application of a combination of peracetic acid, hydrogen peroxide, and water to a surface in which the pesticide formulation is in contact.

In the present invention, the peracetic acid, hydrogen peroxide, and water combination ("biocide combination") is used to reduce or eliminate the growth of microorganisms in the pesticide formulation. Biocides are well known in the art. Typical commercial biocides include: (i) Minncare, which is a peracetic acid solution used as a disinfectant for reverse osmosis membranes; (ii) Proxel GXL, which is an aqueous solution of dipropylene glycol and 17% 1,2-benzisothiazolin-2-one; and (iii) Legend MK, which includes 1.15% 5-chloro-2-methyl-4-isothiazolin-3-one and 0.35% 2-methyl-4-isothiazolin-3-one.

In the present invention, a biocide combination is added to a pesticide suspension to reduce or eliminate the growth of microorganisms in the suspension. The biocide combination constitutes from about 3.0% to about 7.0% by weight of peracetic acid, from about 19.0% to about 25.0% by weight of hydrogen peroxide, and the remainder, from about 68% to about 78% by weight, is water. The total composition by weight of the peracetic acid, hydrogen peroxide, and water, is 100%. The biocide combination is added to the pesticide suspension in an amount such that it comprises from about 0.05% to about 1.0% by weight of the pesticide suspension.

The pesticide is selected from the group consisting of an insecticide, a fungicide, and a herbicide. Suitable insecticides include the heterocyclic compounds described in U.S. Pat. Nos. 5,852,012; 5,719,146; 4,849,432; and 4,742,060; which are incorporated herein by reference. Further, in a preferred embodiment of the invention, the insecticide is a chloronicotinyl or a chlorothiazole. Moreover, insecticides of the following general formulas (I), (II) and (Ill) are most preferred.

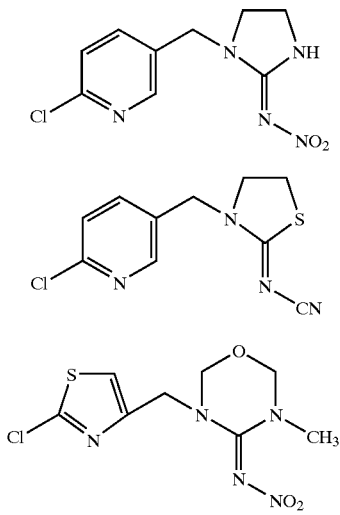

A preferred fungicide is tebuconazole, and a preferred herbicide is metribuzin.

Further, in an embodiment of the present invention, the biocide combination is applied to the interior surface of the vessel in which the pesticide formulation is contained. The method of application may be performed using any manual or automated means known in the art.

In another embodiment of the present invention, the biocide combination is applied to a surface in which the pesticide suspension is in contact. The method of application to the surface may be accomplished using any manual or automated means known in the art.

Having thus described our invention, the following examples are given as being illustrative thereof; and they are in no way meant to be limiting of the specification and the claims. All weights and percentages given are parts by weight or percentages by weight, unless otherwise indicated.

EXAMPLES

Example 1

A study was conducted to demonstrate the effectiveness of adding a peracetic acid, hydrogen peroxide, and water combination ("biocide combination") to inhibit or eliminate the growth of microorganisms in a water-based pesticide suspension concentrate (PROVADO 1.6F). The biocide combination was added in an amount such that it constituted from about 0.0% to about 0.1% by weight of the pesticide suspension. The study was also conducted to evaluate the potential for re-growth of the bacteria after the pesticide suspension was treated with the biocide combination. The biocide combination comprised 4%-by weight of peracetic acid, 20% by weight of hydrogen peroxide, and the remainder was water. Using a jiffy mixer, 0.05% of the biocide combination was added to a first sample of PROVADO 1.6F, and 0.1% of the biocide combination was added to a second sample of PROVADO 1.6F. A third sample was contained in a jug which had been sprayed with approximately 0.1% of the biocide combination prior to filling with the pesticide suspension. A fourth sample was a control sample which contained no biocide combination. All of the samples also contained 0.5% Proxel GXL.

Each of these 4 samples was divided into 8 separate samples, stored at a temperature of 30° C., and then tested for bacterial growth on a weekly basis over an 8 week period.

Initially, the control sample had approximately 11,000 cfu/ml bacteria and the other samples had no initial bacterial contamination. None of these samples were inoculated. There was no growth of bacteria after 8 weeks in any of the samples treated with the biocide combination. The results are shown in Table 1.

TABLE 1

| | Bacteria Present/ml | | | |
|---|---|---|---|---|
| Week | 1 | 2 | 3 | 4 |
| Sample | | | | |
| Jug-treated; 0.1% | 0/ml | 0/ml | 0/ml | 0/ml |
| Suspension-treated; 0.05% | 0/ml | 0/ml | 0/ml | 0/ml |
| Suspension-treated; 0.1% | 0/ml | 0/ml | 0/ml | 0/ml |
| Untreated | 11,000/ml | 8,000/ml | 4,000/ml | 1,000/ml |
| | Bacteria Present/ml | | | |
| Week | 5 | 6 | 7 | 8 |
| Sample | | | | |
| Jug-treated; 0.1% | 0/ml | 0/ml | 0/ml | 0/ml |
| Suspension-treated; 0.05% | 0/ml | 0/ml | 0/ml | 0/ml |
| Suspension-treated; 0.1% | 0/ml | 0/ml | 0/ml | 0/ml |
| Untreated | 0/ml | 0/ml | 0/ml | 0/ml |

Example 2

A study was conducted to demonstrate the effectiveness of adding from about 0.1% to about 1.0% by weight of a biocide combination (comprising 4% by weight of peracetic acid, 20% by weight of hydrogen peroxide, and the remainder water) to inhibit or eliminate the growth of microorganisms in a water-based pesticide suspension concentrate (ADMIRE 2F). The ADMIRE 2F samples contained bacteria that were specific to the production site. Of the six samples, three samples contained bacteria of the pseudomonas species and the other three samples contained bacteria of the flavobacterium species. To the first sample of ADMIRE 2F was added 1.0% of the biocide combination; to the second sample of ADMIRE 2F was added 0.5% of the biocide combination; and to a third sample of ADMIRE 2F was added 0.1% of the biocide combination. The bacteria present in these three samples was of the pseudomonas species. To a fourth sample of ADMIRE 2F was added 1.0% of the biocide combination; to a fifth sample of ADMIRE 2F was added 0.5% of the biocide combination; and to a sixth sample of ADMIRE 2F was added 0.1% of the biocide combination. The bacteria present in these three samples were of the flavobacterium species.

Initially, all of the ADMIRE 2F samples had approximately $1 \times 10^6$ cfu/ml bacteria present. The samples were tested at 1, 2 and 3 hour intervals. The results are shown in Table 2.

TABLE 2

| Biocide Conc. | Bacteria Species | Bacteria Present/ml Time (hrs) | | | |
|---|---|---|---|---|---|
| | | 0 | 1 | 2 | 3 |
| 1.0% | pseudo | $1 \times 10^6$/ml | 0/ml | 0/ml | 0/ml |
| 0.5% | pseudo | $1 \times 10^6$/ml | 0/ml | 0/ml | 0/ml |
| 0.1% | pseudo | $1 \times 10^6$/ml | 0/ml | 0/ml | 0/ml |
| 1.0% | flavo | $1 \times 10^6$/ml | 0/ml | 0/ml | 0/ml |
| 0.5% | flavo | $1 \times 10^6$/ml | 0/ml | 0/ml | 0/ml |
| 0.1% | flavo | $1 \times 10^6$/ml | 0/ml | 0/ml | 0/ml |

Although the invention has been described in detail in the foregoing for the purpose of illustration, it is to be understood that such detail is solely for that purpose and that variations can be made therein by those skilled in the art without departing from the spirit and scope of the invention except it may be limited by the claims.

What is claimed is:

1. A process for inhibiting the growth of microorganisms in a pesticide suspension, comprising the step of:

adding an effective amount of a biocide combination to a pesticide suspension, wherein said biocide combination comprises from about 3.0% to about 7.0% by weight of peracetic acid, from about 19.0% to about 25.0% by weight of hydrogen peroxide, and from about 68% to about 78% by weight of water, wherein the total composition by weight of said biocide combination is 100%.

2. The process of claim 1 wherein the biocide combination comprises from about 0.05% to about 1.0% by weight of the pesticide suspension.

3. The process of claim 1 or 2 wherein the pesticide suspension comprises a pesticide selected from the group consisting of an insecticide, a herbicide, and a fungicide.

4. The process of claim 3 wherein the insecticide is selected from the group consisting of chloronicotinyls and chlorothiazoles.

5. The process of claim 3 wherein the insecticide is a compound selected from the group consisting of
a compound represented by the formula (I)

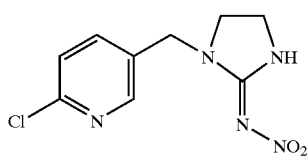

(I)

a compound represented by the formula (II)

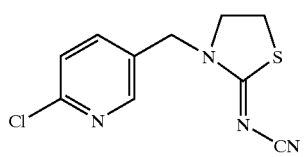

(II)

and a compound represented by the formula (III)

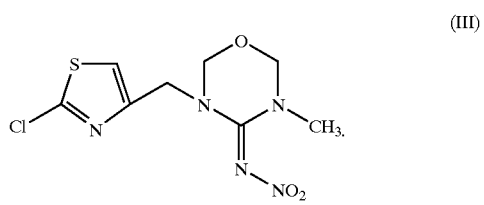

(III)

6. The process of claim 3 wherein the herbicide is metribuzin.

7. The process of claim 3 wherein the fungicide is tebuconazole.

8. A process for inhibiting the growth of microorganisms in a pesticide suspension within a container that contains the pesticide suspension, the pesticide suspension including a pesticide suspended in a liquid medium comprising the steps of:

applying an effective amount of a biocide combination to one or more interior surfaces of a container which one or more surfaces contact a pesticide suspension when said pesticide suspension is contained within said container; and introducing said pesticide suspension into said container, whereupon said pesticide suspension contacts said one or more interior surfaces having said biocide combination applied thereon;

wherein said biocide combination comprises from about 3.0% to about 7.0% by weight of peracetic acid, from about 19.0% to about 25.0% by weight of hydrogen peroxide, and from about 68% to about 78% by weight of water, wherein the total composition by weight of said biocide combination is 100%.

9. The process of claim 8 wherein the biocide combination comprises about 0.05% to about 1.0% by weight of the pesticide suspension.

10. The process of claim 8 or 9 wherein the pesticide suspension comprises a pesticide selected from the group consisting of an insecticide, a herbicide, and a fungicide.

11. The process of claim 10 wherein the insecticide is selected from the group consisting of chloronicotinyls and chlorothiazoles.

12. The process of claim 10 wherein the insecticide is a compound selected from the group consisting of
a compound of the formula (I)

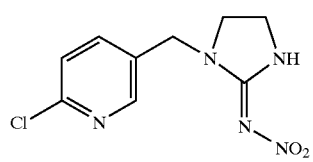

(I)

a compound of the formula (II)

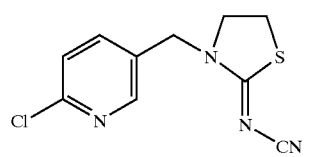

(II)

and a compound of the formula (III)

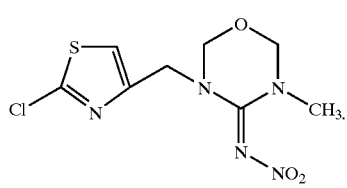

(III)

13. The process of claim 10 wherein the herbicide is metribuzin.

14. The process of claim 10 wherein the fungicide is tebuconazole.

15. A process for inhibiting the growth of microorganisms in a pesticide suspension, comprising the step of applying an effective amount of a biocide combination of peracetic acid, hydrogen peroxide, and water to a surface wherein the pesticide suspension is in contact with the surface.

16. The process of claim 15 wherein the biocide combination comprises from about 0.05% to about 1.0% by weight of the pesticide suspension.

17. The process of claim 15 or 16 wherein the biocide combination comprises from about 3.0% to about 7.0% by weight of peracetic acid, from about 19.0% to about 25.0% by weight of hydrogen peroxide, and from about 68% to about 78% by weight of water, wherein the total composition by weight is 100%.

18. The process of claim 15 wherein the pesticide suspension comprises a pesticide selected from the group consisting of an insecticide, a herbicide, and a fungicide.

19. The process of claim 18 wherein the insecticide is selected from the group consisting of chloronicotinyls and chlorothiazoles.

20. The process of claim 18 wherein the insecticide is a compound selected from the group consisting of a compound of the formula (I)

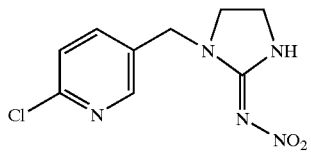

(I)

a compound of the formula (II)

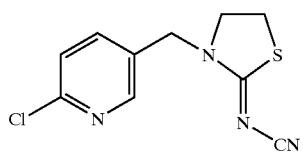

(II)

and a compound of the formula (III)

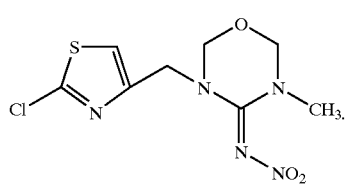

(III)

21. The process of claim 18 wherein the herbicide is metribuzin.

22. The process of claim 18 wherein the fungicide is tebuconazole.

23. A process for inhibiting the growth of microorganisms in a pesticide suspension, comprising the steps of:

a) providing a container for containing a pesticide suspension;

b) applying a biocide combination of peracetic acid, hydrogen peroxide, and water to one or more surfaces of said container that will contact said pesticide suspension when said pesticide suspension is contained within said container; and c) introducing said pesticide suspension into said container, whereupon said pesticide suspension contacts at least one of said surfaces having said biocide combination applied thereto.

24. The process of claim 23 wherein the biocide combination comprises from about 0.05% to about 1.0% by weight of the pesticide suspension.

25. The process of claim 23 wherein the biocide combination comprises from about 3.0% to about 7.0% by weight of peracetic acid, from about 19.0% to about 23.0% by weight of hydrogen peroxide, and from about 68% to about 78% by weight of water, wherein the total composition by weight is 100%.

26. The process of claim 23, 24 or 25 wherein the pesticide suspension comprises a pesticide is selected from the group consisting of an insecticide, a herbicide, and a fungicide.

27. The process of claim 26 wherein the insecticide is selected from the group consisting of chloronicotinyls and chlorothiazoles.

28. The process of claim 26 wherein the insecticide is a compound selected from the group consisting of a compound of the formula (I)

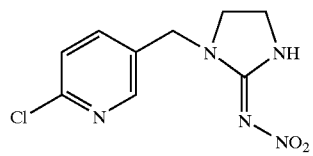

(I)

a compound of the formula (II)

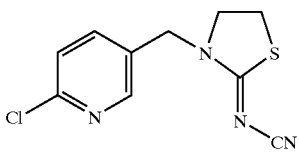

and a compound of the formula (III)

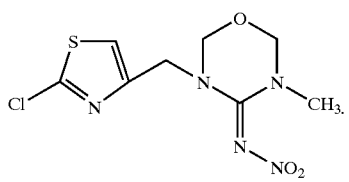

29. The process of claim 26 wherein the herbicide is metribuzin.

30. The process of claim 26 wherein the fungicide is tebuconazole.

31. A process for inhibiting the growth of microorganisms in a pesticide suspension, comprising the steps of:
   a) providing one or more surfaces;
   b) applying a biocide combination of peracetic acid, hydrogen peroxide, and water to at least a portion of at least one surface of said one or more surfaces;
   c) contacting one or more of said portions of said one or more surfaces having said biocide combination applied thereto with a pesticide suspension.

32. The process of claim 31 wherein the biocide combination comprises from about 0.05% to about 1.0% by weight of the pesticide suspension.

33. The process of claim 31 wherein the biocide combination comprises from about 3.0% to about 7.0% by weight of peracetic acid, from about 19.0% to about 23.0% by weight of hydrogen peroxide, and from about 68% to about 78% by weight of water, wherein the total composition by weight is 100%.

34. The process of claim 31, 32 or 33 wherein the pesticide suspension comprises a pesticide selected from the group consisting of an insecticide, a herbicide, and a fungicide.

35. The process of claim 34 wherein the insecticide is selected from the group consisting of chloronicotinyls and chlorothiazoles.

36. The process of claim 34 wherein the insecticide is a compound selected from the group consisting of
a compound of the formula (I)

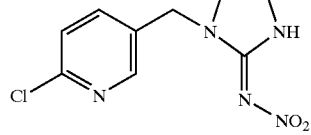

a compound of the formula (II)

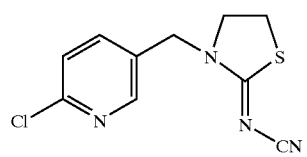

and a compound of the formula (III)

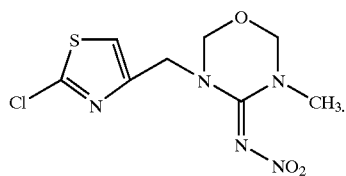

37. The process of claim 34 wherein the herbicide is metribuzin.

38. The process of claim 34 wherein the fungicide is tebuconazole.

* * * * *